United States Patent [19]
Davies

[11] Patent Number: 5,834,317
[45] Date of Patent: *Nov. 10, 1998

[54] METHOD FOR ANTENATAL RISK ASSESSMENT FOR FETAL ABNORMALITIES USING GESTATIONAL AGE DISCREPANCY

[75] Inventor: Christopher John Davies, Caerphilly, United Kingdom

[73] Assignee: Johnson & Johnson Clinical Diagnostics, Inc., Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 584,786

[22] Filed: Jan. 11, 1996

Related U.S. Application Data

[63] Continuation of Ser. No. 217,461, Mar. 24, 1994, abandoned.

[30] Foreign Application Priority Data

Mar. 26, 1993 [GB] United Kingdom .................... 9306354

[51] Int. Cl.⁶ .......................... G01N 33/53; G01N 33/74; G01N 33/76
[52] U.S. Cl. ................................ 436/510; 435/6; 435/7.1; 435/806; 436/65; 436/86; 436/87; 436/814; 436/906
[58] Field of Search ........................ 435/6, 806; 436/510, 436/65, 86, 87, 814, 906

[56] References Cited

U.S. PATENT DOCUMENTS 5,324,668  6/1994  Macri ....................................... 436/518

FOREIGN PATENT DOCUMENTS

89/00696  2/1989  WIPO .

OTHER PUBLICATIONS

Tim Reynolds et al.: "Utility of Unconjugated Estriol in Screening for Down Syndrome is Not Proven" Clinical Chemistry, 39:9, pp. 2023–2025, 1993.

Tim Reynolds and Rhys John: "Comparison of Assay Kits for Unconjugated Estriol Shows That Expressing Results as Multiples of the Median Causes Unacceptable Variation in Calculated Risk Factors for Down Syndrome" Clinical Chemistry, 38:9, pp. 1888–1892, 1992.

Reynolds et al., 1990. The mathematical basis of multivariate risk screening with special reference to screening for Down's syndrome associated pregnancy. Annals of Clinical Biochemistry 27 (Part 5):452–458.

Lockwood et al., 1987. A sonographic screening method for Down syndrome. Am. J. Obstet. Gynecol. 157: 803–808.

Sorokin et al., 1991. Postmortem chorionic villus sampling correlation of cytogenetic and ultrasound findings. Am. J. Med. Genetics 39(3):314–316.

Crossley et al., 1991. Prenatal screening for chromosome abnormalities using maternal serum chorionic gonadotrophin, alpha–fetoprotein, and age. Prenatal Diagnosis 11:83–101.

*Primary Examiner*—James C. Housel
*Assistant Examiner*—James L. Grun

[57] ABSTRACT

A method for antenatal screening for chromosomal and other abnormalities in an unborn child is determined by measuring the gestational age discrepancy of the pregnant mother. This data is determined (a) by reference to the last menstrual period, and (b) a biometric measurement of the fetus. The difference between the ages as determined using (a) and (b) is calculated. This calculated difference is then examined using reference data to determine fetal abnormalities. These data can also be used with assay of maternal fluids for various pregnancy markers.

7 Claims, 12 Drawing Sheets

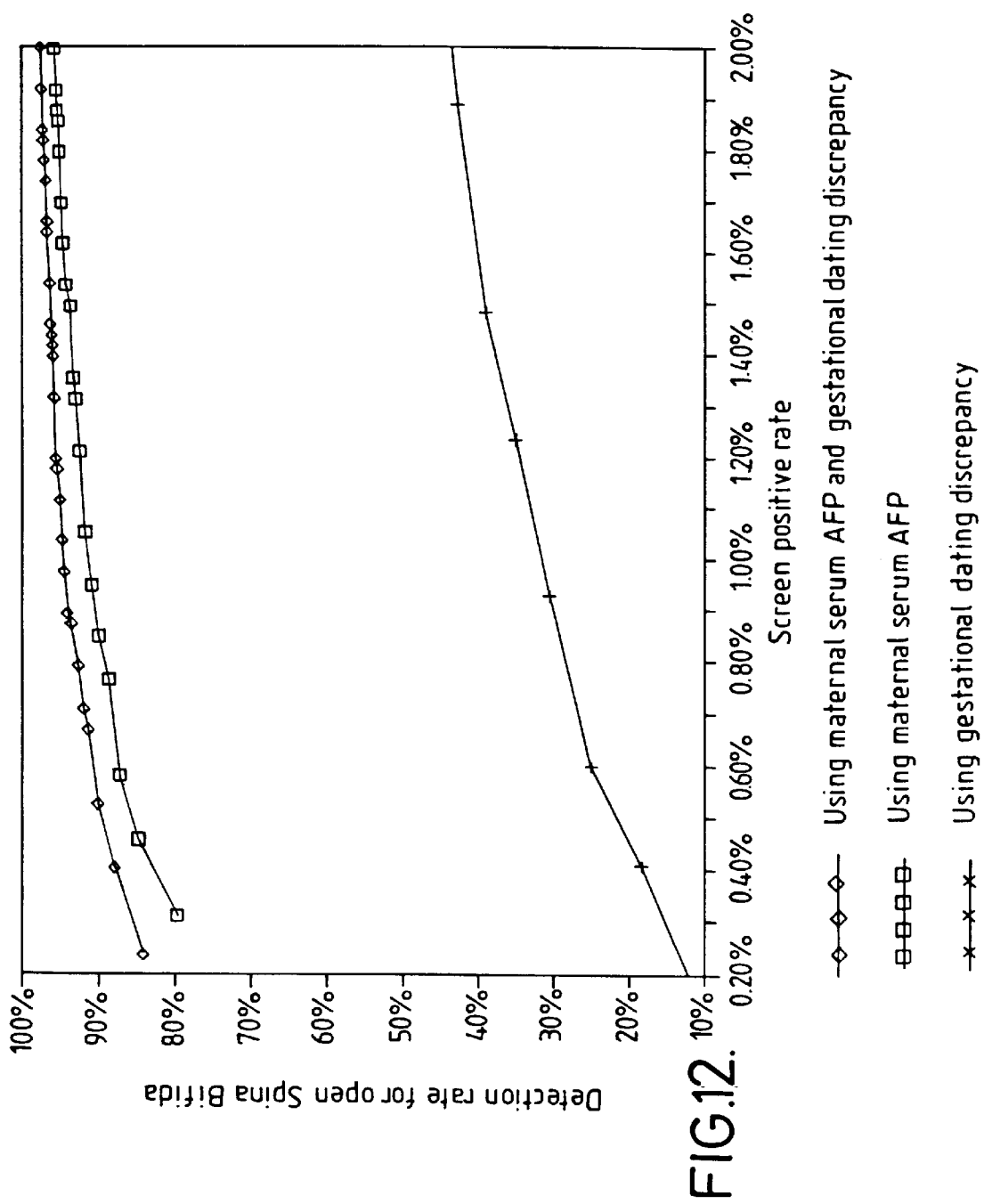

METHOD FOR ANTENATAL RISK ASSESSMENT FOR FETAL ABNORMALITIES USING GESTATIONAL AGE DISCREPANCY

This is a continuation of application Ser. No. 08/217,461, filed Mar. 24, 1994, now abandoned, which is hereby incorporated by reference.

FIELD OF THE INVENTION

This invention relates to a method for antenatal screening for chromosomal abnormalities and to an apparatus for performing the method.

BACKGROUND OF THE INVENTION

The risk of Down Syndrome and some other chromosomal abnormalities in an unborn child is known to increase with the age of the mother and it is this knowledge which forms the basis for selection of pregnant women for further investigation. Further investigation in the case of Down Syndrome involves sampling of the amniotic fluid by amniocentesis, a procedure which itself carries a risk for the mother of the unborn child, induction of a miscarriage being a known hazard of this procedure.

Maternal serum markers for Down Syndrome are widely used for antenatal screening for this chromosomal abnormality, the most common of these markers being alpha-fetoprotein (AFP), human chorionic gonadotropin (hCG)—either the intact molecule thereof or its free beta subunit—and unconjugated estriol (UE). Details relating to the use of these markers, which may be used in combination with maternal age, in antenatal screening for Down Syndrome are provided, for example, in U.S. Pat. No. 4,874,693, WO 89/00696 and WO 90/08325.

U.S. Pat. No. 5,100,806 discloses the use of the free beta subunit of hCG as a marker in antenatal screening for Edwards Syndrome.

One method of prenatal screening for fetal Down Syndrome in the second trimester of pregnancy uses a combination of maternal age and maternal serum AFP, hCG and UE. In fetal Down Syndrome, the maternal serum concentrations of AFP and UE are slightly lower than in normal pregnancies, when the concentrations are expressed relative to the median concentration found in unaffected pregnancies at the same age of gestation (termed the "multiple of the median" in unaffected pregnancies or "MoM"). In contrast, the concentration of maternal serum hCG MoM is higher in Down Syndrome affected pregnancies. The concentrations of all three markers (as log MoM) are approximately Gaussian distributed and the distributions for unaffected and affected pregnancies overlap. The overlap in values is such that it is impossible to choose a cut-off point which will clearly discriminate between the two populations.

Knowledge of the concentration of each analyte is of considerable value. Rather than revealing to which population the sample value belongs, it reveals the probability of the sample being taken from a particular population. The principles involved can be demonstrated by a graph of frequency against MoM (log scale) such as FIG. 1 which relates to AFP as marker. This demonstrates the principles involved in calculating the likelihood that a sample has come from a Down Syndrome affected pregnancy, in this case for maternal serum AFP, although the same principle applies to hCG, UE or any marker, biochemical or otherwise in which the distributions in affected and unaffected pregnancies differ.

More information can be gained by combining markers than by using them individually. There is no theoretical limit to the number of markers which can be combined and the principle and practice of combining them is well known statistically. For Down Syndrome screening the likelihood ratio is derived from the two trivariate normal distributions for unaffected and affected pregnancies using maternal serum AFP, UE and hCG. Maternal age is another marker for Down Syndrome, the risk being much higher in older women. As none of the serum markers has been shown to be related to any of the maternal serum analytes, then by Baye's theorem the final combined risk of having a child with Down Syndrome for an individual woman is obtained by multiplying the likelihood that the maternal serum markers' values belong to an affected population by the a priori age risk.

The final combined risk may then be used to counsel women about their risk. If the judgement is that the risk is high, then they may wish to proceed to amniocentesis so that fetal cells may be obtained and a firm diagnosis made. The amniocentesis procedure carries with it a risk of miscarriage on the order of 0.5% to 1.0%. Thus for a woman with a combined risk of Down Syndrome of 1:400, her risk of losing the baby through the amniocentesis is higher than her risk of having a child with Down Syndrome. Conversely a woman with a combined risk of 1:10, may feel that the risk is high enough to warrant amniocentesis.

It has been estimated that selecting the 5% of women screened and found to have the highest risk would enable detection of approximately 60% of Down Syndrome affected pregnancies.

It is therefore desirable to develop improved methods of antenatal screening for chromosomal abnormalities.

SUMMARY OF THE INVENTION

According to the present invention, a method for antenatal screening for abnormalities in a fetus, Comprises determining the gestational age of a pregnant woman (a) by reference to the last menstrual period dates and (b) by a biometric measurement of the fetus, the difference between the ages as determined in (a) and (b) being calculated and the calculated difference then examined using reference data to determine fetal chromosomal abnormalities.

Further, the present invention provides an apparatus comprising means adapted for receiving measurements relating to a fetus carried by a pregnant woman and computer means for comparing the measurements to reference data to determine fetal abnormalities wherein the measurements relate to the difference between the gestational age of the woman as determined (a) by reference to the last menstrual period dates and (b) by a biometric measurement of the fetus.

The invention has the advantage that it enables the detection rate for fetal abnormalities to be increased using information which is routinely collected from many women.

BRIEF DESCRIPTION OF THE DRAWINGS

FIG. 12 is referred to in Example 10 and is a graph of detection rate for Open Spina Bifida against screen-positive rate.

DETAILED DESCRIPTION OF THE INVENTION

Figure 1:
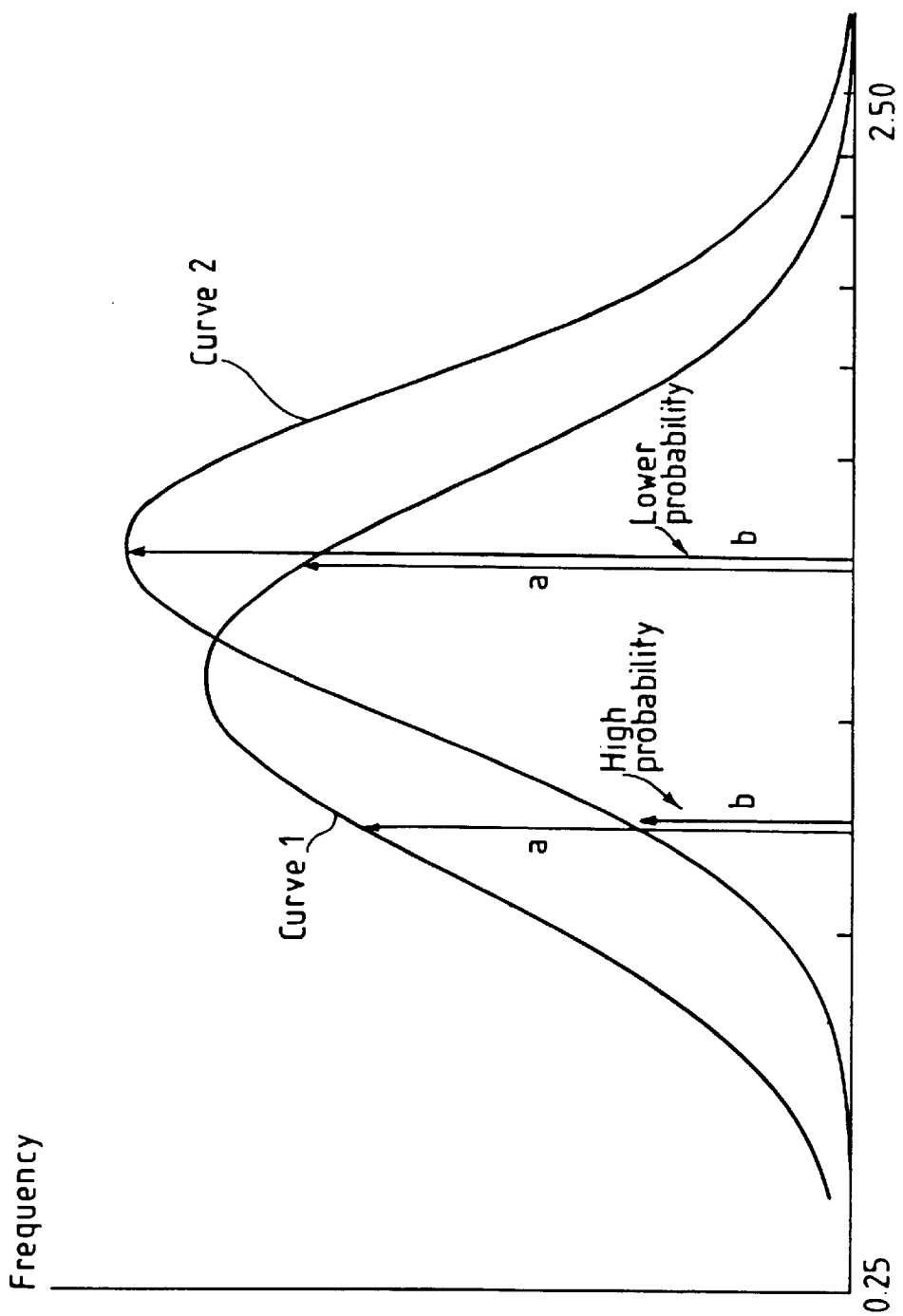
FIG. 1 is a graph of Frequency against AFP MoM (on a log scale) which shows the distribution of maternal serum AFP in a Down Syndrome pregnancy (Curve 1) and in a normal pregnancy (Curve 2).

Some chromosomal and other abnormalities show growth retardation in a fetus, i.e. the fetus is not as large as would be expected from the gestational age. Gestational age is usually estimated from the date of the last menstrual period. It can also be determined by a biometric measurement of the fetus. Usually biometric measurements are made using ultrasonography but other means are possible, for example nuclear magnetic resonance (NMR).

The most common estimate of gestational age by biometric measurement using e.g. ultrasonography is derived from measurement of the distance between the parietal lobes, the biparietal diameter (BPD). Other measurements that can be made include crown to rump, humerus, orbit to orbit, abdominal circumference, ear size and femur length. Of these measurements, the crown to rump measurement is usually made during the first trimester of pregnancy while the other measurements are best made later during the second trimester. The preferred measurement to be made using ultrasonography in the method of the invention varies to some extent depending upon the chromosomal defect which is to be detected.

In the determination of the gestational age from the last menstrual period, the calculation is made using the elapsed days since the first day of the last menstrual period.

If the gestational age assessed by biometric measurement is significantly less than that calculated from the last menstrual period, there is the possibility that intra-uterine growth retardation has occurred. There are, however, other possible causes of such a discrepancy, the most notable being that the date of the last menstrual period has not been determined accurately.

The method of the invention can be used for antenatal screening for a wide range of chromosomal abnormalities. It is particularly useful for detection of Edwards Syndrome (Trisomy 18), Open Spina Bifida and Patau Syndrome (Trisomy 13). Other abnormalities which may be detected include Down Syndrome (Trisomy 21), Turner Syndrome (Monosomy X) and Kleinefelter's Syndrome. The method of the invention may be used to screen for individual abnormalities or to screen for groups of abnormalities together. For example, it could be used to screen for both Trisomy 18 and Open Spina Bifida.

The method of the invention can be used in combination with measurement of one or more other markers such as maternal age, gestational age and/or one or more components of a maternal fluid including urine, saliva, cerebrospiral fluid and in particular serum markers from maternal blood samples (from plasma or whole blood) using multivariate analysis. In particular, it can be used together with measurement of the serum markers intact human chorionic gonadotropin (hCG), free beta hCG, and pregnancy associated plasma protein A (PAPPA). Other markers which may be measured include alpha-fetoprotein (AFP), unconjugated estriol (UE), progesterone (Pr), 16-alpha-hydroxy-dehydroepiandrosterone sulfate (16-alpha-hydroxy-DHEAS) and dehydroepiandrosterone sulfate (DHEAS), intact inhibin (In) and its subunits, Schwangerschaft Protein 1 (SP1), free alpha subunit of hCG and precursors and metabolites of these markers. Thus one or more of these other markers may be measured together with the principal markers used in the method of the invention. For example, the method of the invention may be used with the gestational ages, hCG (intact molecule, or free alpha or free beta subunits), PAPPA and AFP as the markers to be measured.

The method of the invention is suitably carried out in the period from 8 to 22 weeks of pregnancy with the period from 14 to 22 weeks being preferred.

Figure 2:
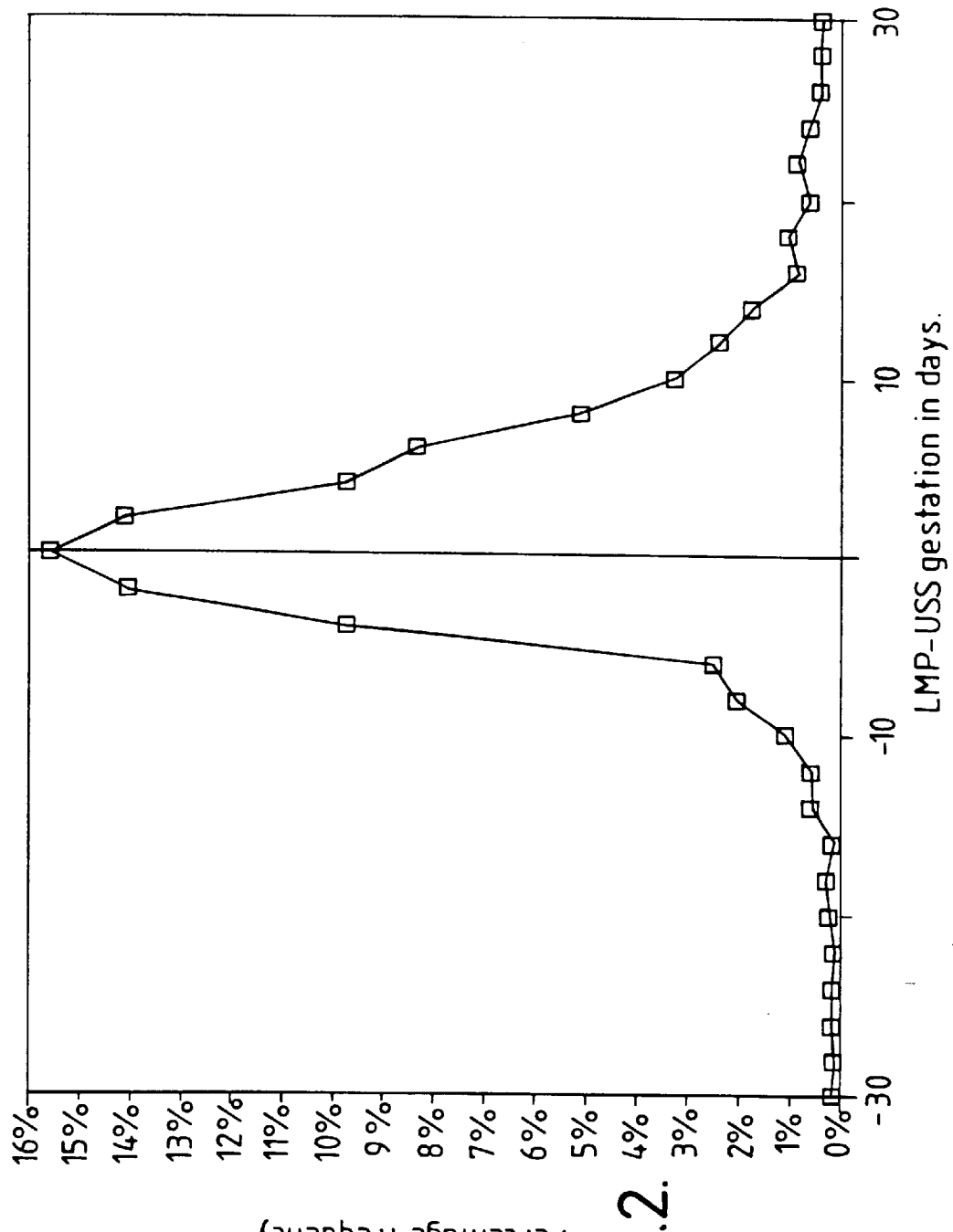
FIG. 2 is a graph of percentage frequency against the gestational discrepancy, i.e. the difference in days between the gestational ages determined by reference to the last menstrual period and by biometric measurement—in this case by ultrasonography.

FIG. 2 is the result of a clinical trial conducted at 6 centers throughout Europe from which 1761 pregnancies of known normal outcome were identified which had gestational age determined by ultrasound biometry and by reference to the last menstrual period. It shows that the difference in gestational ages (in days) between the ages as determined by reference to the last menstrual period and by biometric measurement (ultrasonography)—termed the gestational discrepancy—has an approximately Gaussian distribution of values. The mean value of approximately +3 days reflects the fact that more women will mistakenly overestimate their gestational ages than will mistakenly underestimate them, and that the dates determined using ultrasonography are constructed from formulae derived from women with well characterized dates for their last menstrual periods.

Figure 3:
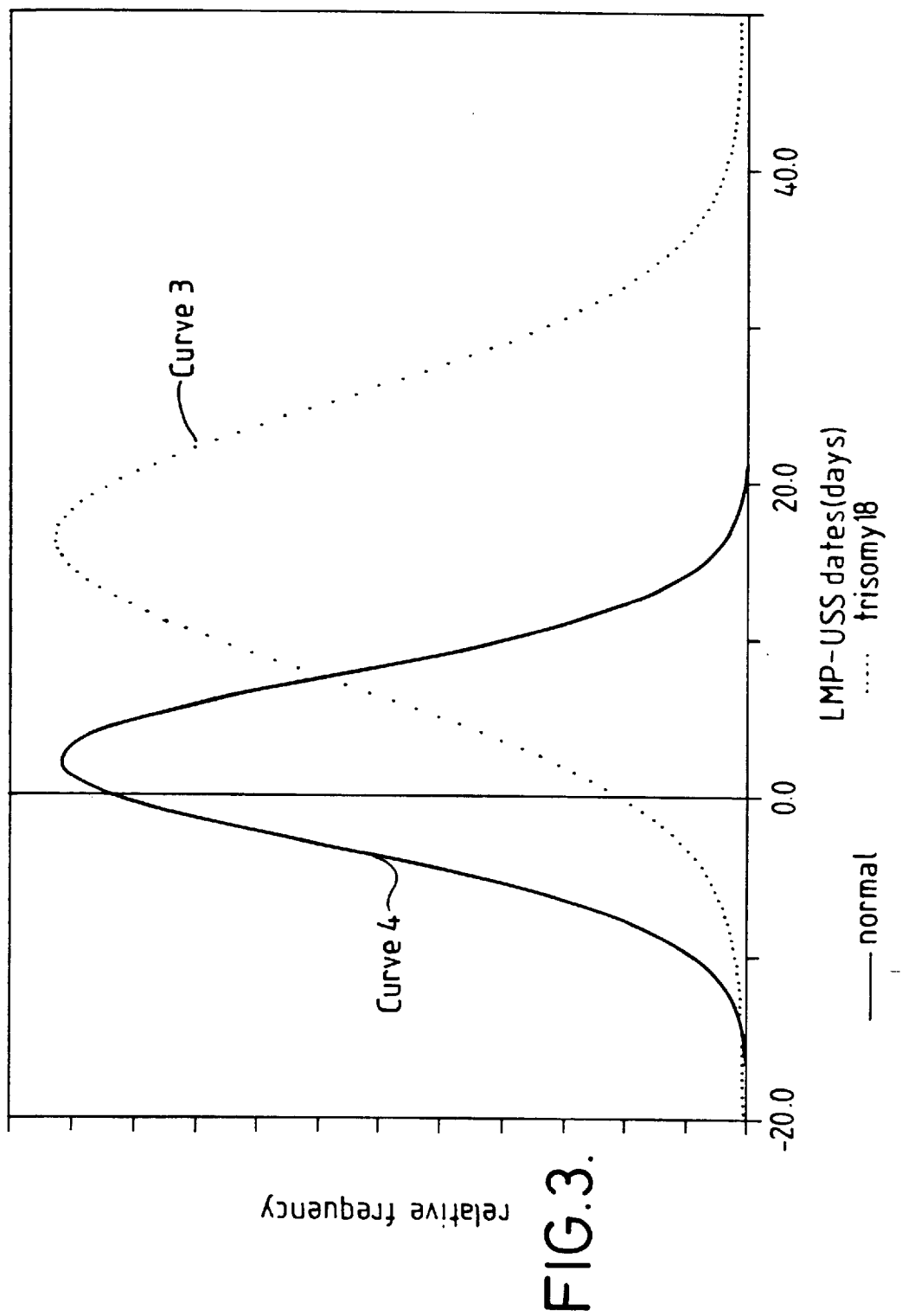
FIG. 3 is referred to in Example 1 and is a graph of relative frequency and gestational discrepancy (as in FIG. 2) showing the difference between a Trisomy 18 affected pregnancy (Curve 3) and an unaffected pregnancy (Curve 4).

If a chromosomal or other abnormality is associated with growth retardation then the Gaussian distribution of values will be shifted to the right. For example fetuses with Trisomy 18 are known on average to show a discrepancy in gestational ages of approximately 2 weeks. The two overlapping distributions of dating discrepancies are as shown in FIG. 3. These two overlapping distributions are completely analogous to those with maternal serum markers, for example with AFP as shown in FIG. 1.

It is possible therefore to derive a likelihood ratio that a given discrepancy in dates is due to Trisomy 18, or to another abnormality associated with intra-uterine growth retardation, in an exactly analogous manner to that illustrated for maternal serum AFP in FIG. 1.

Furthermore, it is possible to combine the discrepancies in gestational ages with other biochemical or other markers for the abnormality, in a multivariate calculation of risk, since it is known for example that maternal serum hCG, UE and AFP are all lower in uncomplicated Trisomy 18 pregnancies. The principle of combining several markers for fetal abnormality in multivariate models has been described by Reynolds and Penney (*Ann.Clin.Biochem.*, 27, 452–458, 1990).

The present invention has been discussed generally in relation to Trisomy 18, but other chromosomal abnormalities are also associated with intra-uterine growth retardation, for example Open Spina Bifida, Triploidy and Turner Syndrome. All of these abnormalities have associated maternal serum biochemical markers. Other markers used need not be restricted to maternal serum, but may also be measured in amniotic fluid.

The following examples are provided for illustrative purposes only, and the invention is not to be construed as limited thereto.

EXAMPLE 1

As part of large multicenter trials in the United Kingdom and elsewhere in Europe, 7 cases of Trisomy 18 and 521 unaffected maternal serum control samples were identified. All samples were measured for maternal serum AFP, hCG and UE. In each case the gestational ages were known both by reference to the last menstrual period and by fetal biometry of the biparietal diameter. All three analytes measured change with gestational age. From the control data, regressions were performed of the unaffected median value at each gestational week, versus the ultrasound measured gestation in weeks, weighted by the number of contributory samples at each week. For AFP and UE, this took the form of a linear regression of the natural log of the MoM value $\{\ln(\text{MoM})\}$, versus gestational age in days. For hCG, it took the form of an exponential decay.

Using these regression equations, each analyte value from both Trisomy 18 and unaffected samples was divided by the unaffected median value for that gestational day, the latter being derived from the regression equations.

Table 1 gives the details of the Trisomy 18 cases. Table 2 gives a summary of the statistical analysis of the Trisomy 18 cases together with the 521 control samples. There was no statistically significant difference in standard deviations between the controls and Trisomy 18 cases. The standard deviations were therefore pooled. The gestational age discrepancy was calculated as last menstrual period derived gestation in days (LMP)—ultrasound derived gestation in days (USS).

TABLE 1

Women with Trisomy 18 affected pregnancies

| Patient ID | USS | LMP | LMP-USS 1U/ml | AFP MoM | AFP ln(MoM) | AFP |
|---|---|---|---|---|---|---|
| BO211 | 101 | 119 | 18 | 22.93 | 0.830 | −0.186 |
| BO250 | 136 | 155 | 19 | 61.87 | 1.192 | 0.176 |
| BO289 | 115 | 140 | 25 | 34.85 | 0.980 | −0.020 |
| BO340 | 115 | 120 | 5 | 33.08 | 0.930 | −0.072 |
| BO379 | 113 | 141 | 28 | 18.42 | 0.537 | −0.622 |
| GO346 | 108 | 117 | 9 | 13.54 | 0.432 | −0.839 |
| GO347 | 136 | 145 | 9 | 28.56 | 0.550 | −0.597 |

TABLE 2

Statistical parameters

|  | Trisomy 18 | Unaffected Control |
|---|---|---|
| n | 7 | 521 |
| mean | 16.14 | 2.197 |
| pooled standard deviation | 4.65 | 4.65 |

It can be seen that there is a marked difference in the distribution of the gestational age discrepancy between the Trisomy 18 cases and the controls. The Trisomy 18 cases show on average 16.1 days earlier gestation when assessed by ultrasound biometry than by LMP dating.

The discrepancies in dating were found to approximate to a Gaussian distribution for both Trisomy 18 cases and controls. These Gaussian distributions are shown in FIG. 3.

This shows that there is a likelihood that a given gestational age discrepancy forms part of either the Gaussian distribution for Trisomy 18 or unaffected values can be calculated in an analogous fashion as is demonstrated for the use of maternal serum AFP in the assessment of Down Syndrome risk in FIG. 1.

EXAMPLE 2

The calculation of an individual woman's risk of having a child with Trisomy 18 during the second trimester of pregnancy using the measured discrepancy in gestational ages is shown below.

For a 37 year old woman, her age related risk can be derived from epidemiological studies such as those reported by Crossley (Crossley etal, *Prenatal Diagnosis*, 11, pages 83–102, 1991).

Age risk=1:245

This risk is modified according to the likelihood ratio derived from analysis of the gestational age discrepancy between USS and LMP derived gestations as shown in the following Table 3. The final combined risk is calculated by dividing the right hand side of the risk odds ratio (245) by the likelihood ratio.

TABLE 3

Individual risks using gestational age discrepancy and prior age-related risk for Trisomy 18 at second trimester for a 37 year old woman
Age risk = 1:245

| gestational age discrepancy in days | likelihood ratio | combined risk |
|---|---|---|
| −2 | 0.0007 | 1:344014 |
| 0 | 0.0026 | 1:92737 |
| 2 | 0.0098 | 1:25000 |
| 4 | 0.0364 | 1:6739 |
| 6 | 0.1349 | 1:1817 |
| 8 | 0.5003 | 1:490 |
| 10 | 1.8558 | 1:132 |
| 12 | 6.8841 | 1:36 |
| 14 | 25.5368 | 1:10 |
| 16 | 94.7303 | 1:3 |

EXAMPLE 3

Figure 4:
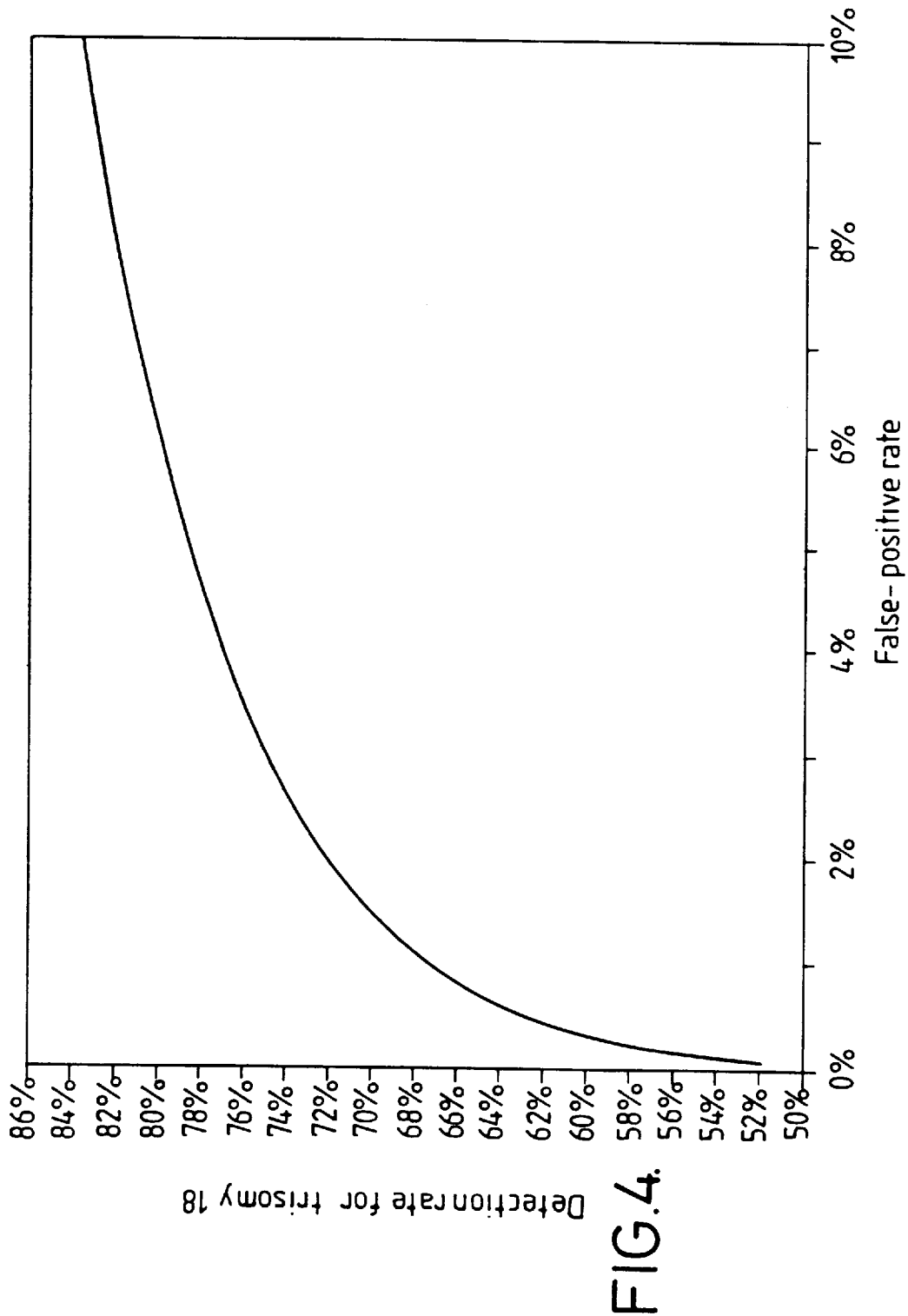
FIG. 4 is referred to in Example 3 and is a graph of detection rate for Trisomy 18 against false-positive rate.

The utility of any screening test is best described by the Receiver Operating Characteristics (ROC). This shows the relationship between the sensitivity (the proportion of Trisomy 18 cases that would be detected at a given risk cut-off level) and the specificity (the proportion of unaffected women who would be categorized incorrectly as being at high risk of Trisomy 18, i.e. the false-positive rate). The ROC curve for screening using the discrepancy in gestational age dating is shown in FIG. 4.

Table 4 shows the interpolated values from this ROC curve showing the sensitivity of the screening test at various false positive rates.

TABLE 4

Detection rates for given false positive rate: Trisomy 18: gestational age discrepancy alone

| false-positive rate | detection rate |
| --- | --- |
| 1.0% | 76.2% |
| 2.0% | 83.9% |
| 3.0% | 87.8% |
| 4.0% | 90.2% |
| 5.0% | 92.0% |

EXAMPLE 4

Several maternal serum biochemical markers may be used in screening for Trisomy 18. For example alphafetoprotein (AFP), unconjugated estriol (UE), human chorionic gonadotrophin (hCG), the free beta and alpha subunits of human chorionic gonadotrophin ((hCG), pregnancy associated placental protein A (PAPPA) are all known to be decreased in pregnancies where the fetus has Trisomy 18. AFP levels are raised in Trisomy 18 affected pregnancies where the fetus also has an associated neural tube defect.

None of the Trisomy 18 cases described in Table 1 was also affected by neural tube defects.

The AFP concentrations, multiple of the median levels (MoM) and the natural log of the AFP MoM levels [ln(AFP MOM)], are shown in Table 1. The statistical summary of the AFP data for both the Trisomy 18 cases and the unaffected controls are shown in Table 5. There was no statistically significant difference in either the standard deviation or the correlations between the controls and Trisomy 18 cases. The correlations and standard deviations were therefore pooled.

TABLE 5

Statistical parameters

| | Trisomy 18 | unaffected controls |
| --- | --- | --- |
| n | 7 | 521 |
| mean ln(AFP MoM) | 0.309 | 0.040 |
| standard deviation ln(AFP MoM) | 0.361 | 0.361 |
| correlation coefficient between ln(AFP MoM) and gestational age discrepancy | 0.135 | 0.135 |

Figure 5:
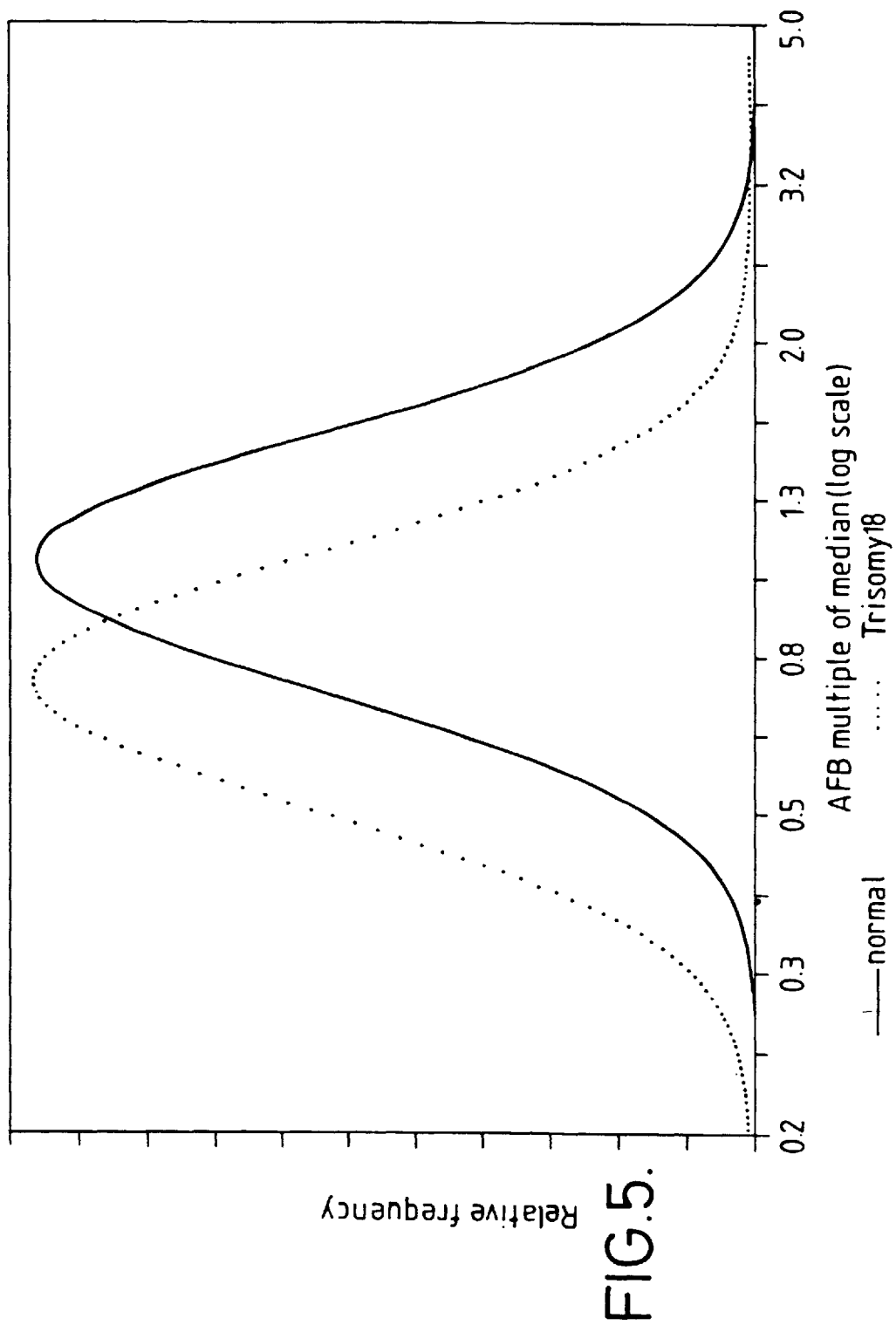
FIG. 5 is referred to in Example 4 and is a graph of relative frequency against AFP multiple of median (log scale).

The Gaussian distributions of ln(AFP MoM) in Trisomy 18 and control pregnancies is shown in FIG. 5. It can be seen that likelihood ratios can be calculated using these distributions in the same manner as was described when screening for Down Syndrome using maternal AFP, exemplified in FIG. 1.

The calculation of an individual woman's risk of having a child with Trisomy 18 at the time of screening is shown below.

Age related risk for 37 year old woman=1:245.

The risk is modified according to the likelihood ratio derived from analysis of the maternal serum AFP level, expressed as the MoM value, as shown in Table 6. The final combined risk is calculated by dividing the right hand side of the risk odds ratio (in this case 245) by the likelihood ratio.

TABLE 6

Individual risks using maternal serum AFP and prior age related risk of 1:245 for Trisomy 18, at second trimester for a 37 year old woman

| AFP MoM | likelihood ratio | combined risk |
| --- | --- | --- |
| 0.5 | 4.4857 | 1:55 |
| 1.0 | 0.6982 | 1:351 |
| 2.0 | 0.1087 | 1:2255 |
| 3.0 | 0.0366 | 1:6694 |

Figure 6:
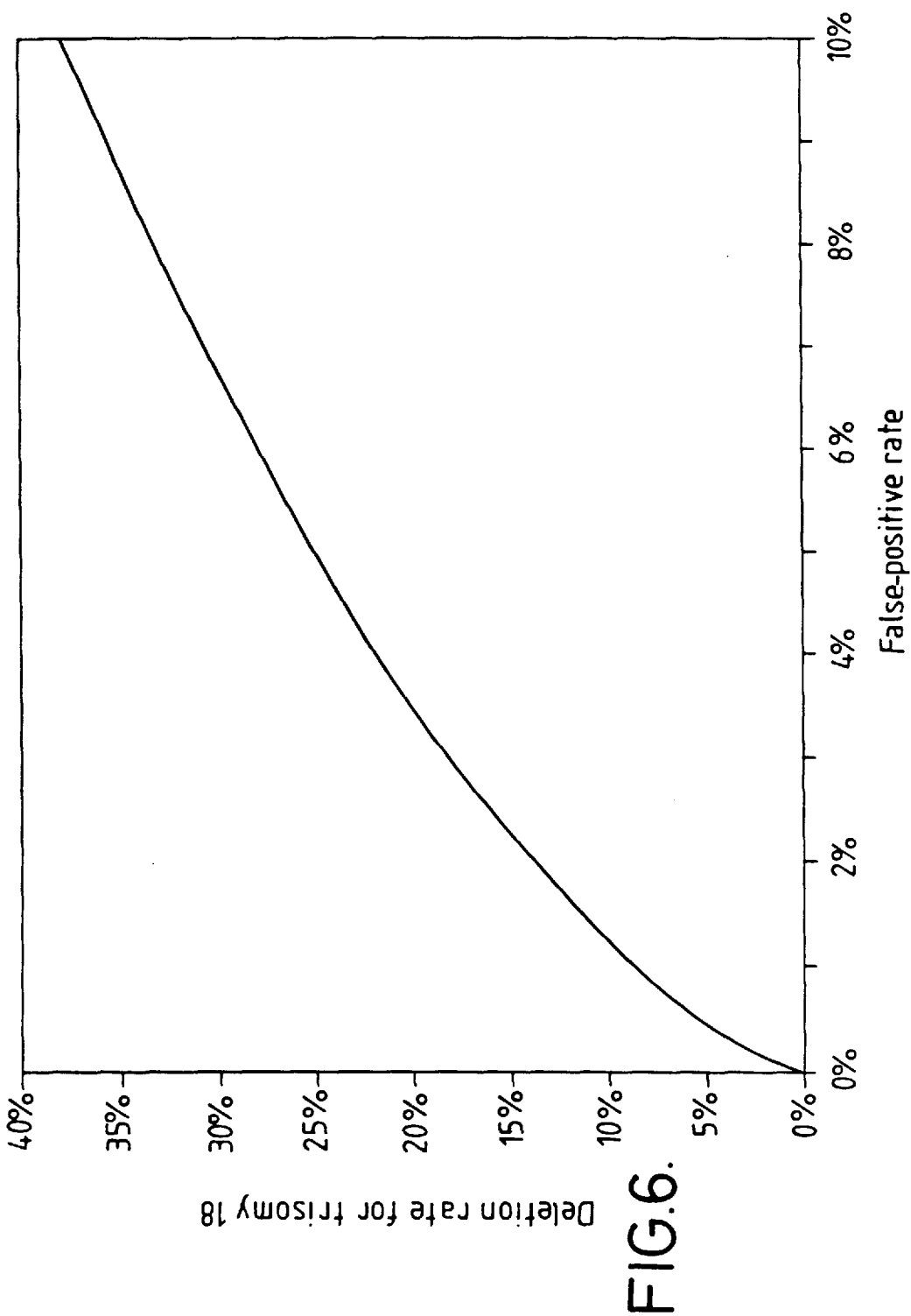
FIG. 6 is referred to in Example 4 and is a graph of detection rate for Trisomy 18 against false-positive rate.

The ROC curve for screening for Trisomy 18 using maternal serum AFP is shown in FIG. 6. Table 7 shows the interpolated values from this ROC curve showing the sensitivity of the screening test at various false positive rates.

TABLE 7

Detection rates for given false positive rate, Trisomy 18, maternal serum AFP alone

| 1-specificity (false-positive rate) | sensitivity (detection rate) |
| --- | --- |
| 1.0% | 8.8% |
| 2.0% | 13.9% |
| 3.0% | 18.1% |
| 4.0% | 21.7% |
| 5.0% | 25.0% |

EXAMPLE 5

The optimal method of combining screening tests is to use them simultaneously by calculating the likelihood ratio from a multivariate, rather than univariate, Gaussian distribution. The use of multivariate Gaussian distributions in calculating risk assessments for Down Syndrome has been described by Reynolds (*Annals of Clinical Biochemistry*, 27, 452–458, 1990).

Knowledge is required of the correlation between the screening markers to allow for their dependence. The statistical parameters in Tables 2 and 5 show the mean and standard deviations and correlations for ln(AFP MoM) and for the gestational age discrepancies.

By way of illustration, the risks assigned to a 37 year old woman with various levels of maternal serum AFP and different gestational age dating discrepancies is shown in Table 8.

TABLE 8

Individual risks for a 37 year old woman for Trisomy 18, using AFP and gestational age discrepancy combined with maternal age risk of 1:245 at second trimester
Age related risk for 37 year old woman = 1:245

| AFP MoM | gestational age discrepancy | combined likelihood ratio | combined risk |
| --- | --- | --- | --- |
| 0.5 | 0 | 0.0161 | 1:15199 |
| 0.5 | 2 | 0.0649 | 1:3776 |
| 0.5 | 6 | 1.0510 | 1:233 |
| 0.5 | 10 | 17.0267 | 1:14 |
| 0.5 | 16 | 1110.1926 | 2:1 |
| 1.0 | 0 | 0.0572 | 1:226025 |
| 1.0 | 2 | 0.0829 | 1:56156 |

TABLE 8-continued

Individual risks for a 37 year old woman for Trisomy 18, using AFP and gestational age discrepancy combined with maternal age risk of 1:245 at second trimester
Age related risk for 37 year old woman = 1:245

| AFP MoM | gestational age discrepancy | combined likelihood ratio | combined risk |
|---|---|---|---|
| 1.0 | 6 | 0.2237 | 1:3466 |
| 1.0 | 10 | 0.8419 | 1:214 |
| 1.0 | 16 | 11.4713 | 1:3 |
| 3.0 | 0 | 0.0021 | 1:16303001 |
| 3.0 | 2 | 0.0032 | 1:4050525 |
| 3.0 | 6 | 0.0093 | 1:250034 |
| 3.0 | 10 | 0.0375 | 1:15434 |
| 3.0 | 16 | 0.5691 | 1:237 |

EXAMPLE 6

Screening Performance In the Ordinary Population

The estimates of risks in Example 5 do not allow for the performance of such a test were it applied as a routine screening test in the general population. In such circumstances the incidence of the disorder must be taken into account in the general population. Such estimates can be derived by integrating the bivariate Gaussian distribution of the discrepancy of gestational age dating and maternal serum AFP over the age distribution of pregnancies. The age related risk of Trisomy 18 varies with the age of the mother and age related risk factors have been published based on epidemiological surveys, see e.g. Crossley et al, *Prenatal Diagnosis*, 11, 83–102, 1990).

The age distribution of pregnancies in England and Wales (Office of Population Census and Surveys, Birth Statistics 1987–1989, HMSO) for the years 1986–1988 were averaged and used as a reference population for this study. Repeated sets of 10,000 sample bivariate Gaussian distributions according to the statistical parameters described in Tables 2 and 5, for unaffected and Trisomy 18 affected populations were generated using the statistical package MINITAB™ software. Likelihood ratios were calculated for the use of gestational age discrepancy only, for maternal serum AFP only and using both tests combined according to the principle described by Reynolds and Penney (*Annals of Clinical Biochemistry*, 27, 452–458, 1990) and the statistical parameters described in Tables 2 and 5. The simulated screening performance was estimated for a range of risk cut-off levels, below which a woman would be considered to be at sufficiently high risk to be offered the diagnostic tests of amniocentesis and fetal karyotyping. For each maternal age the likelihood ratio below which a woman at that age would be screen-positive was calculated. The proportion of likelihood ratios for unaffected or affected pregnancies above this limit were then calculated. These figures represent the percentage of women at that specific age who would be at higher risk than the cut-off (screen-positive), for unaffected or Trisomy 18 affected pregnancies respectively. Multiplication of these proportions by the actual numbers of unaffected or Trisomy 18 affected pregnancies at that maternal age gave the actual numbers of women. The procedure was repeated for all maternal ages and the numbers of affected and unaffected women who would be screen-positive obtained by summation of the numbers at each maternal age. The procedure was repeated for a range of risk-cut off values.

These data provided estimates of the detection rate (proportion of women with Trisomy 18 affected pregnancies who have risks higher than the cut-off value) and the corresponding false-positive rate (proportion of unaffected pregnancies who have risks higher than the cut-off value).

Figure 7:
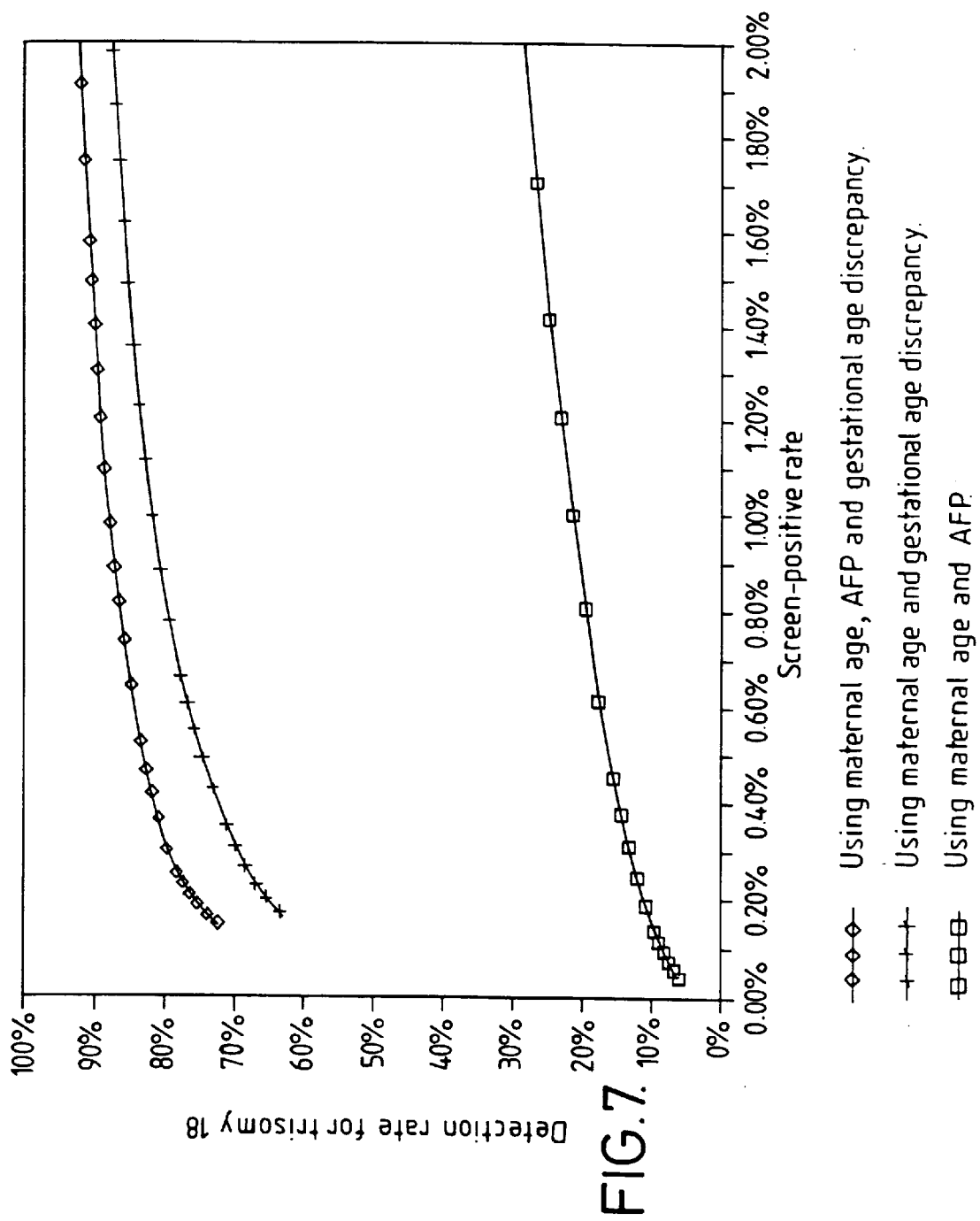
FIG. 7 is referred to in Example 6 and is a graph of detection rate for Trisomy 18 against screen-positive rate.

Such data enabled an ROC curve to be constructed showing the relationship between the screen-positive rate and detection rate should a test be applied routinely to all pregnant women in England and Wales. This ROC curve is shown in FIG. 7. The ROC curve illustrates the additional increase in detection for the same false-positive rate when markers are combined in this fashion. Extrapolated detection rates for given false-positive rates are shown below in Table 9.

TABLE 9

Detection rates for Trisomy 18 at specified false positive rates

| 1-Specificity (false-positive rate) | Sensitivity Maternal age & AFP | Sensitivity Maternal age & gestational age discrepancy | Sensitivity Maternal age, gestational age discrepancy & AFP |
|---|---|---|---|
| 0.5% | 16.2% | 74.4% | 83.3% |
| 1.0% | 21.4% | 81.8% | 88.0% |
| 1.5% | 25.3% | 85.3% | 90.3% |
| 2.0% | 28.4% | 87.4% | 92.2% |

Thus for example if the test is applied routinely to the general population then 92.2% of Trisomy 18 cases can be identified, while performing amniocentesis and fetal karyotyping on only 2% of the population at highest risk.

EXAMPLE 7

Extension Using Other Serum Analytes

Maternal serum hCG and maternal serum UE are known to be lowered in Trisomy 18 affected pregnancies. Table 10, which presents information additional to Table 1, shows the individual maternal serum hCG and UE levels in the Trisomy 18 cases in this study. Table 11 shows the statistical distributions for the natural logarithm of maternal serum hCG {ln(hCG MoM)} and maternal serum UE {ln(UE MoM)} in both unaffected pregnancies and Trisomy 18 affected pregnancies from this study.

TABLE 10

Women with Trisomy 18 affected pregnancies

| Patient ID | hCG IU/ml | UE nmole/l | MoM Values hCG | UE | ln (MoM) hCG | UE |
|---|---|---|---|---|---|---|
| B0211 | 8.89 | 3.31 | 0.199 | 1.020 | −1.613 | +0.019 |
| B0250 | 3.62 | 3.97 | 0.190 | 0.514 | −1.661 | −0.665 |
| B0289 | 8.80 | 1.98 | 0.320 | 0.431 | −1.140 | −0.841 |
| B0340 | 5.11 | 1.81 | 0.186 | 0.394 | −1.684 | −0.931 |
| B0379 | 3.65 | 4.61 | 0.125 | 1.055 | −2.076 | +0.054 |
| G0346 | 13.58 | 1.15 | 0.398 | 0.298 | −0.922 | −1.211 |
| G0347 | 8.43 | 3.88 | 0.443 | 0.503 | −0.815 | −0.688 |

TABLE 11

Statistical parameters for hCG and UE, Trisomy 18 cases and controls using pooled standard deviations

|  | ln(hCG MoM) | ln(UE MoM) |
|---|---|---|
| Mean normal controls | −0.0099 | −0.0212 |
| Mean Trisomy 18 | −1.4159 | −0.6089 |
| Pooled standard deviation | 0.4969 | 0.3349 |

Figure 8:
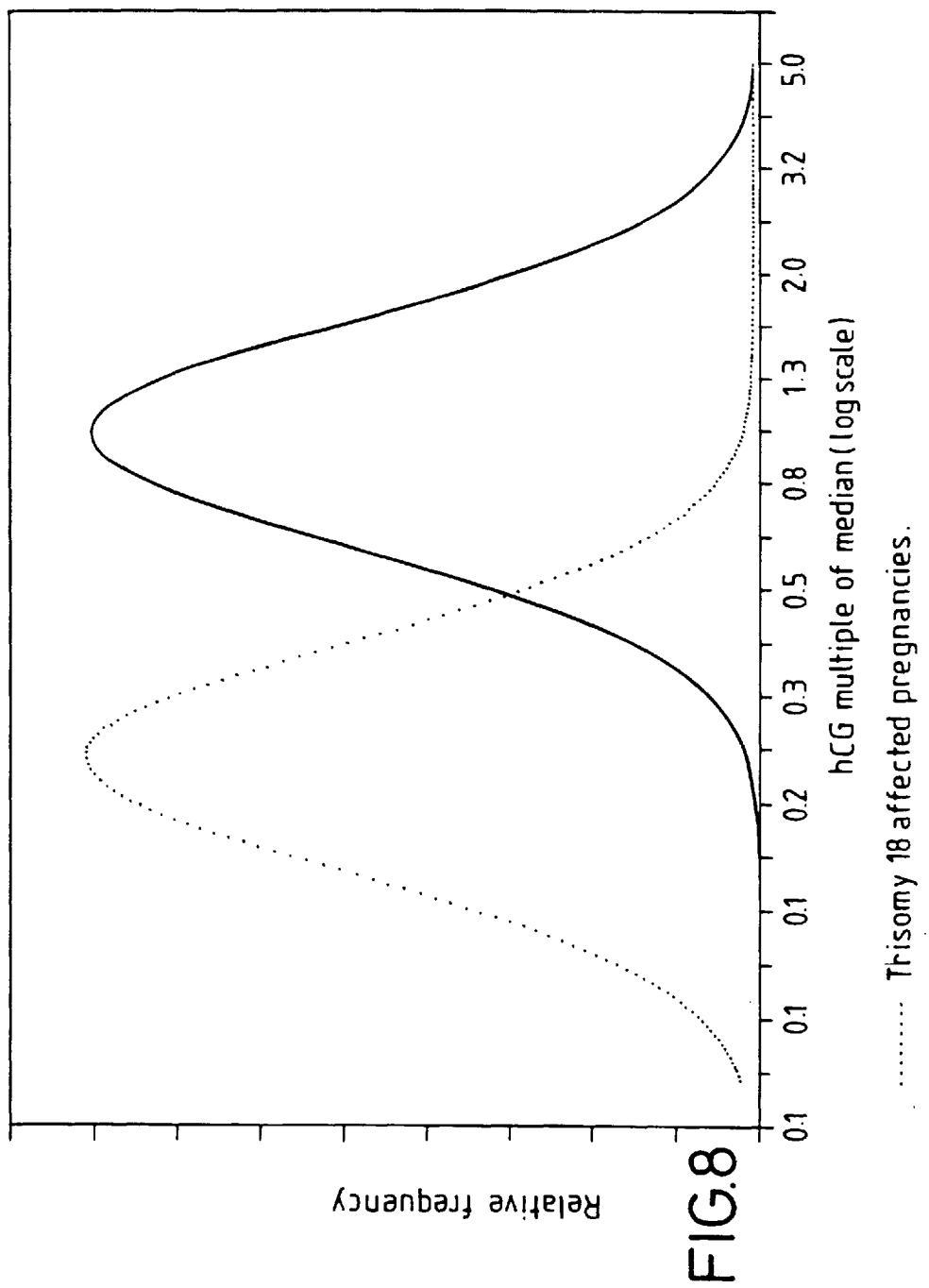
FIGS. 8 and 9 are referred to in Example 7 and are graphs of relative frequency against multiple of median (log scale) for hCG and UE respectively.
Figure 9:
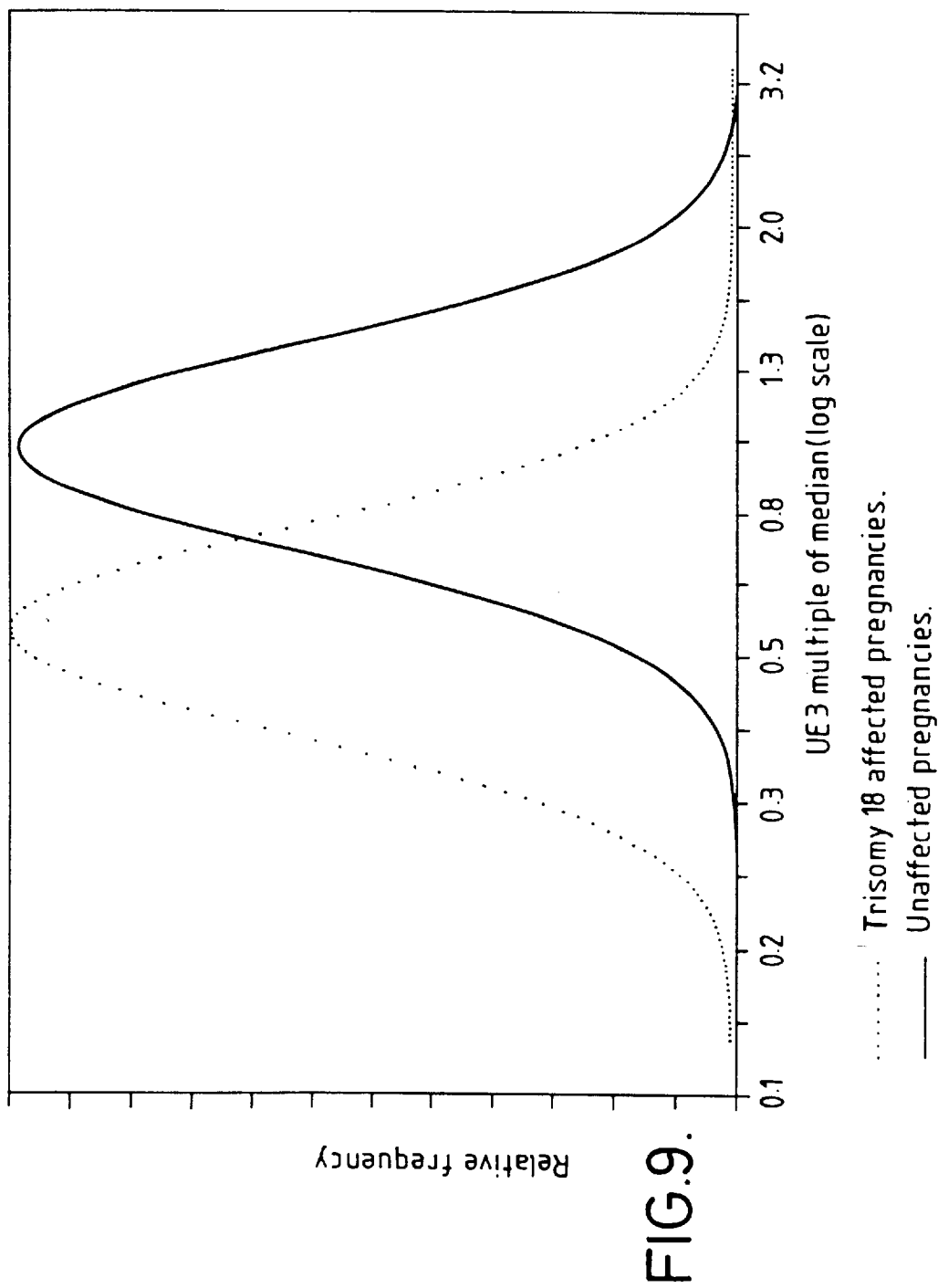

FIGS. 8 and 9 show the Gaussian distributions for ln(hCG MoM) and ln(UE MoM) respectively. Both demonstrate the further potential for the inclusion of such maternal serum markers together with the discrepancy in gestational age dating in multivariate Gaussian models to calculate likelihood ratios. The mathematical combination of multiple screening markers has been described in detail (Reynolds and Penney, *Annals of Clinical Biochemistry*, 27, 452–458, 1990).

Other maternal serum or fetal bimetric measurements could also be included with the gestational age discrepancy in a multivariate model to improve the screening performance further.

EXAMPLE 8

Screening For Open Spina Bifida

Twenty-five cases of Open Spina Bifida were examined as part of the above clinical trials. Maternal serum AFP was measured and MoM values were calculated for both cases and controls as described in Example 1. Table 12 shows the individual data relating to the Open Spina Bifida cases. Table 13 shows the statistical summary of the distributions of gestational age dating discrepancies and the natural logarithm of maternal serum AFP MoM {ln(AFP MoM)}. There was no statistically significant difference in either the standard deviations or correlations between Open Spina Bifida cases and controls and the correlations and standard deviations were therefore pooled.

TABLE 12

Women with Open Spina Bifida affected pregnancies

| Patient ID | GA(days) USS | LMP | LMP-USS | AFP IU/ml | MoM AFP | ln MoM AFP |
|---|---|---|---|---|---|---|
| G0405 | 122 | 129 | 9 | 190.6 | 4.727 | 1.553 |
| NTD021 | 122 | 136 | 15 | 109.4 | 2.713 | 0.998 |
| NTD022 | 129 | 136 | 4 | 216.4 | 4.729 | 1.554 |
| NTD023 | 129 | 129 | 1 | 178.2 | 3.896 | 1.360 |
| NTD024 | 122 | 129 | 9 | 342.4 | 8.489 | 2.139 |
| NTD025 | 115 | 115 | −1 | 103.7 | 2.916 | 1.070 |
| NTD027 | 122 | 136 | 19 | 265.1 | 6.573 | 1.883 |
| NTD028 | 115 | 115 | −2 | 124.9 | 3.514 | 1.257 |
| NTD030 | 122 | 122 | 5 | 144.3 | 3.577 | 1.275 |
| NTD032 | 122 | 129 | 8 | 260.0 | 6.446 | 1.863 |
| NTD033 | 122 | 157 | 37 | 169.6 | 4.205 | 1.436 |
| NTD034 | 122 | 136 | 19 | 286.7 | 7.108 | 1.961 |
| NTD035 | 115 | 136 | 20 | 228.6 | 6.431 | 1.861 |
| NTD036 | 101 | 122 | 23 | 105.9 | 3.834 | 1.344 |
| NTD037 | 115 | 122 | 11 | 91.0 | 2.561 | 0.940 |
| NTD038 | 115 | 122 | 9 | 214.4 | 6.030 | 1.797 |
| NTD039 | 115 | 115 | 6 | 173.1 | 4.868 | 1.583 |
| NTD040 | 136 | 101 | −30 | 123.2 | 2.375 | 0.865 |
| NTD041 | 115 | 122 | 6 | 122.9 | 3.457 | 1.241 |
| NTD043 | 122 | 122 | −5 | 84.0 | 2.083 | 0.734 |
| NTD045 | 122 | 136 | 15 | 197.4 | 4.894 | 1.588 |
| NTD057 | 122 | 136 | 18 | 92.8 | 2.301 | 0.834 |
| NTD059 | 122 | 136 | 12 | 141.5 | 3.507 | 1.255 |
| RA044 | 122 | 136 | 17 | 175.2 | 4.343 | 1.469 |
| RA045 | 122 | 136 | 19 | 217.1 | 5.384 | 1.683 |

TABLE 13

Statistical parameters

|  | Gestational Age Discrepancy | | Natural log AFP MoM | |
|---|---|---|---|---|
|  | OSB | Control | OSB | Control |
| n | 25 | 521 | 25 | 521 |
| mean | 10.30 | 1.97 | 1.422 | 0.041 |
| pooled SD | 4.44 | 4.44 | 0.362 | 0.362 |
| pooled correlation (gestational age discrepancy & natural log AFP MoM) | 0.1490 | 0.1490 | | |

OSB = Open Spina Bifida
SD = Standard Deviation

Figure 10:
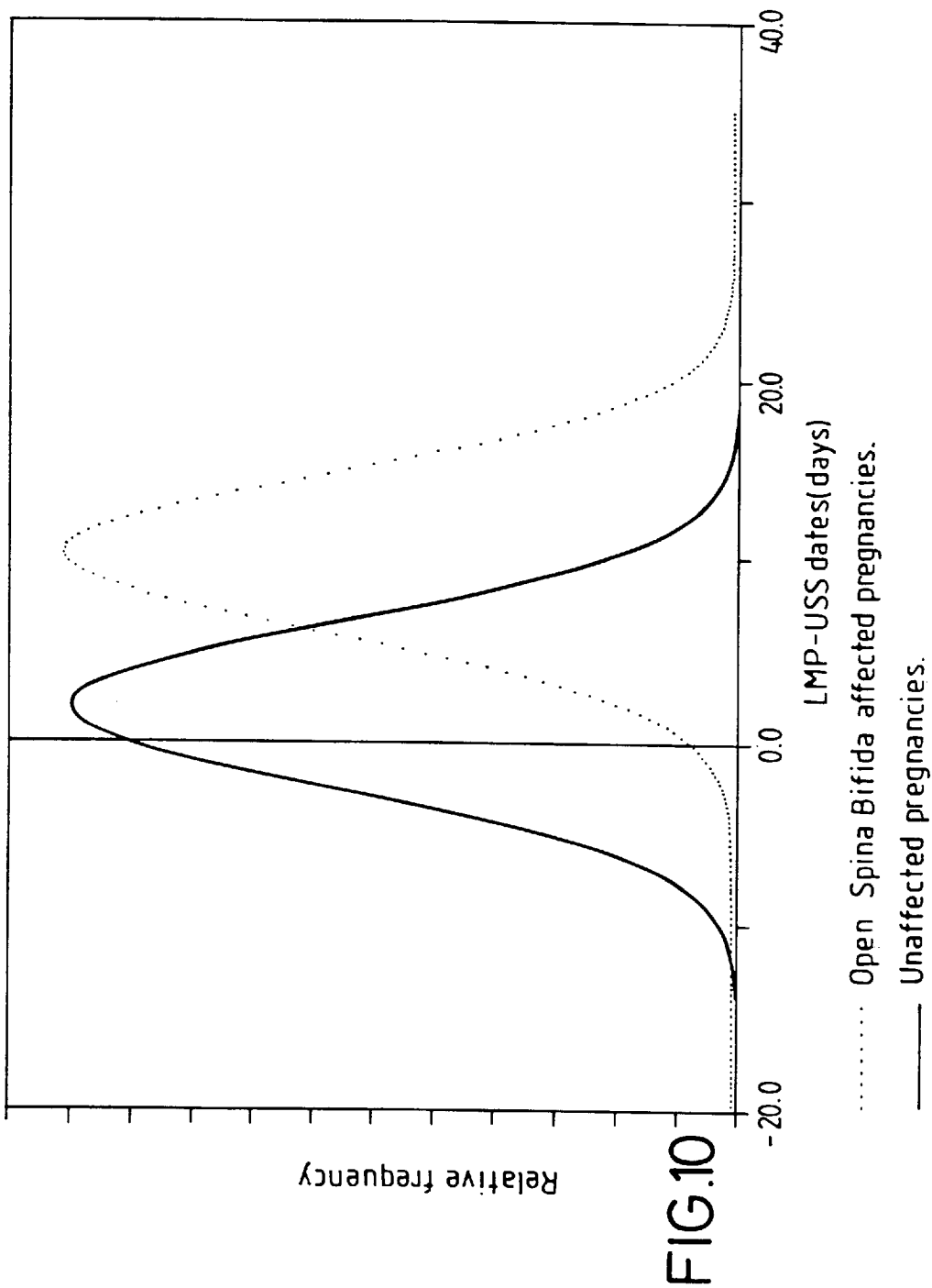
FIG. 10 is referred to in Example 8 and is a graph of relative frequency against LMP-USS (days).

FIG. 10 shows the distribution of gestational age dating discrepancies for Open Spina Bifida and for unaffected control pregnancies. It is apparent that Open Spina Bifida fetuses have a significantly smaller biparietal diameter and hence lower ultrasound estimated gestational age than in control pregnancies.

The discrepancy in gestational age can be used as a marker for Open Spina Bifida in an analogous fashion to its use for Trisomy 18 in Example 1.

Figure 11:
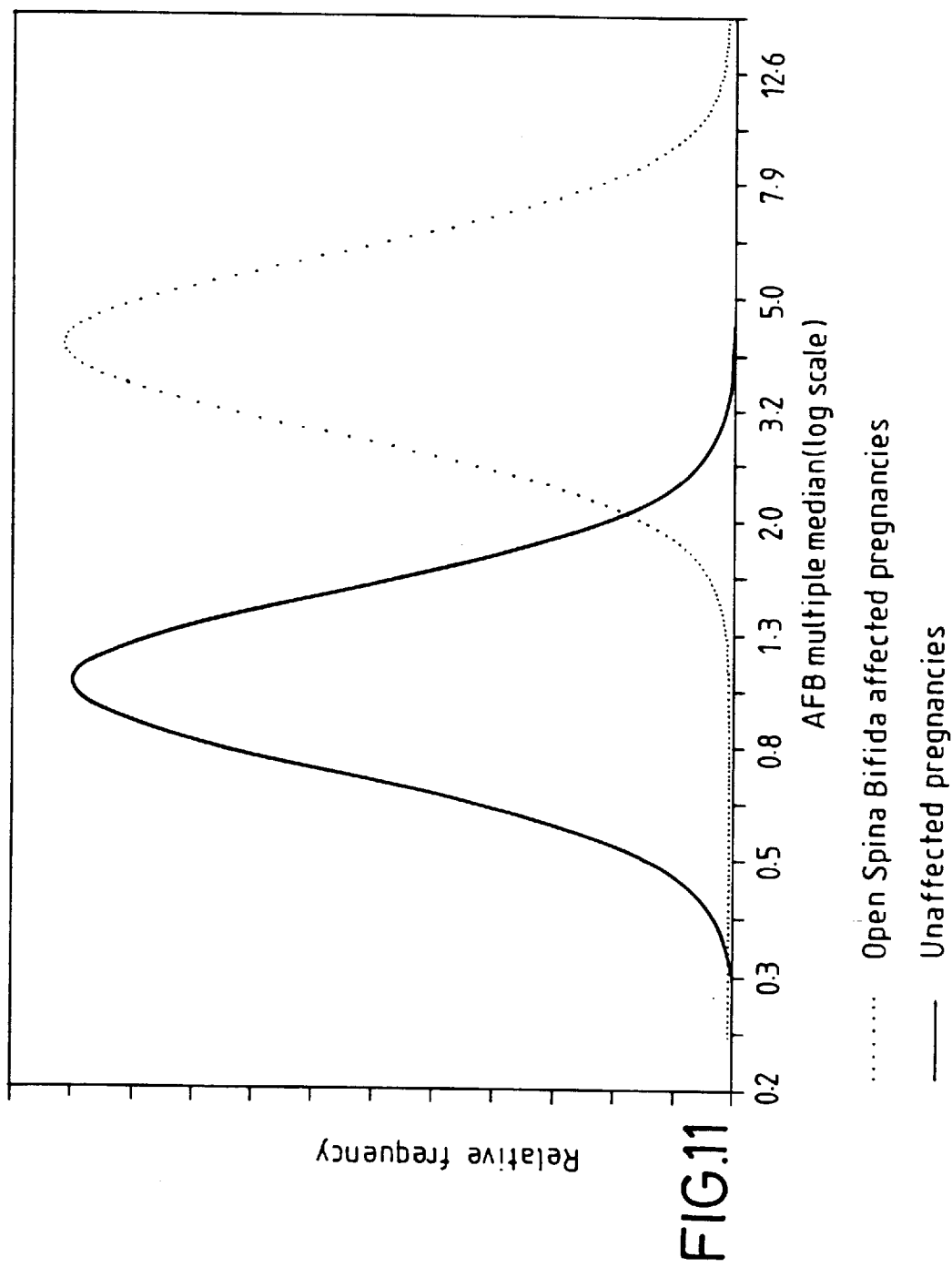
FIG. 11 is referred to in Example 8 and is a graph of relative frequency against AFP multiple of median (log scale).

Maternal serum AFP has been used for many years as a maternal serum marker for Open Spina Bifida. The distribution of ln(AFP MoM) found in this study is shown in FIG. 11. Data are in accord with previously published data.

EXAMPLE 9

Estimating Individual Open Spina Bifida Risk

The background risk of Open Spina Bifida varies temporally, geographically and racially. In addition there are known to be various genetic, social and nutritional determinants of risk. In practice, local epidemiological surveillance is used to determine the background (pre-test) risk. In this example the background risk is assumed to be 1:500.

The background risk is modified according to the likelihood ratio derived from analysis of the gestational age discrepancy between USS and LMP, from analysis of the maternal serum AFP or by using both markers in a bivariate combination. The final risk is calculated by dividing the right hand side of the risk odds ratio (in this case 500) by the likelihood ratio. The modified risks for various combinations of gestational age dating discrepancies and maternal serum AFP MoM alone or in combination are shown in Table 14.

TABLE 14

Individual risks for Open Spina Bifida using AFP and gestational age discrepancy and a priori pre-test risk (incidence) of 1:500

| AFP MoM | Gestational Age Discrepancy | Likelihood Ratio | Final Risk |
|---|---|---|---|
| not used | 0 | 0.0751 | 1:6662 |
| not used | 2 | 0.1745 | 1:2865 |
| not used | 4 | 0.4058 | 1:1232 |
| not used | 8 | 2.1943 | 1:228 |
| not used | 16 | 64.1535 | 1:8 |
| 1.0 | not used | 0.00044 | 1:1126254 |
| 2.0 | not used | 0.66867 | 1:748 |
| 2.5 | not used | 7.05111 | 1:71 |
| 3.0 | not used | 48.32238 | 1:10 |
| 1.0 | 0 | 0.00010 | 1:4765230 |
| 1.0 | 2 | 0.00019 | 1:2612053 |
| 1.0 | 4 | 0.00035 | 1:1431792 |
| 1.0 | 8 | 0.00116 | 1:430206 |
| 1.0 | 16 | 0.01287 | 1:38839 |
| 2.0 | 0 | 0.1080 | 1:4633 |
| 2.0 | 2 | 0.1969 | 1:2540 |
| 2.0 | 4 | 0.3592 | 1:1392 |
| 2.0 | 8 | 0.1953 | 1:418 |
| 2.0 | 16 | 13.2401 | 1:38 |
| 2.5 | 0 | 1.0064 | 1:497 |
| 2.5 | 2 | 1.8361 | 1:272 |
| 2.5 | 4 | 3.3496 | 1:149 |
| 2.5 | 8 | 11.1478 | 1:45 |
| 2.5 | 16 | 123.4804 | 1:4 |
| 3.0 | 0 | 6.2387 | 1:80 |
| 3.0 | 2 | 11.3813 | 1:44 |
| 3.0 | 4 | 20.7633 | 1:24 |
| 3.0 | 8 | 69.1034 | 1:7 |
| 3.0 | 16 | 765.4331 | 1:1 |

EXAMPLE 10

Routine Population Screening Performance Estimate

The predicted performance of a Open Spina Bifida test when applied to the entire population can be estimated in a manner analogous to that demonstrated for screening for Trisomy 18 in Example 6, except that the incidence is not related to maternal age, and hence integration over the maternal age distribution is not required. Repeated sets of 10,000 sample bivariate Gaussian distributions were generated according to the statistical parameters described in Table 13, for unaffected and Open Spina Bifida affected populations. Likelihood ratios were calculated for the use of gestational age discrepancy only, for maternal serum AFP only and using both tests combined. The simulated screening performance was estimated for a range of risk cut-off levels, below that at which a woman is considered to be at sufficiently high risk to be offered the diagnostic test of amniocentesis and/or detailed ultrasonographic examination of the fetal spine. The likelihood ratio above which a woman is screen-positive was calculated. The proportion of likelihood ratios for unaffected or affected pregnancies above this critical likelihood ratio was then calculated from the data for unaffected and affected pregnancies. These proportions represent the percentage of women who are at higher risk than the risk cut-off (screen-positive), for unaffected or Open Spina Bifida pregnancies respectively.

Multiplication of these proportions by the total number of unaffected or Open Spina Bifida pregnancies at that maternal age gave the actual numbers of women. The procedure was repeated for a range of risk cut-off values.

These data provided estimates of the detection rate (proportion of women with Open Spina Bifida affected pregnancies who have risks higher than the cut off value) and the corresponding false-positive rate (proportion of unaffected pregnancies who have risks higher than the cut-off value). Such values enable an ROC curve to be constructed showing the relationship between the screen-positive rate and the detection rate when such a test is applied routinely to all pregnant women in England and Wales. This ROC curve is shown in FIG. 12. The ROC curve illustrates the detection rates predicted using gestational age dating discrepancies (GA) alone, maternal serum AFP alone or both in combination (both combined). Extrapolated detection rates for given false-positive rates are shown in Table 15.

TABLE 15

Detection rate for Open Spina Bifida at specified false positive rates

| | Sensitivity | | |
|---|---|---|---|
| False positive rate | GA Discrepancy Alone | AFP Alone | Both Combined |
| 0.5% | 21.5% | 84.86% | 89.3% |
| 1.0% | 32.1% | 91.2% | 94.4% |
| 1.5% | 38.7% | 94.06% | 96.1% |
| 2.0% | 43.1% | 95.2% | 97.4% |

Table 15 shows that the combination of both gestational age discrepancy and maternal serum AFP as a marker for Open Spina Bifida is better than either test used alone. For example, 91% of cases of Open Spina Bifida can be identified in the 1% of the population at highest risk with maternal serum AFP alone, whilst the addition of gestational age dating discrepancy has the potential to raise this to 94% whilst maintaining the same 1% screen-positive rate.

A further common diagnostic test performed on those women at highest risk is amniocentesis and the measurement of amniotic fluid AFP. Although amniotic fluid AFP measurement is a highly sensitive test, a very small but significant number of women will have a false-positive result. This is particularly distressing as this may lead to the effective termination of a healthy unaffected child by mistake. The use of gestational age dating discrepancies in a bivariate risk calculation with amniotic fluid AFP would also be of benefit in reducing the incidence of such errors.

The invention has been described in detail with particular reference to preferred embodiments thereof, but it will be understood that variations and modifications can be effected within the spirit and scope of the invention.

I claim:

1. A method for assessing antenatal risk for a fetal abnormality, comprising:

A) determining a pregnant patient's pretest risk of carrying a fetus having said abnormality, B) determining a gestational age discrepancy value of the pregnant patient by calculating a difference between gestational age as determined by two methods, the two methods being i) last menstrual period date of the patient, and ii) biometric measurement of the fetus carried by the patient, C) calculating a first probability that the gestational age discrepancy value is part of a Gaussian distribution of gestational age discrepancy values found in pregnancies with said fetal abnormality, D) calculating a second probability that the gestational age discrepancy value is part of a Gaussian distribution of gestational age discrepancy values found in unaffected pregnancies, E) calculating a likelihood ratio, said likelihood ratio being the ratio of said first probability and said second probability, and F) assessing that antenatal risk for said abnormality in the fetus carried by the patient by modifying the patient's pretest risk by the likelihood ratio.

2. The method according to claim 1 wherein said fetal abnormality is selected from the group consisting of Trisomy 18, Trisomy 13, and Open Spina Bifida.

3. A method for assessing antenatal risk for a fetal abnormality, comprising:

A) calculating a pregnant patient's pretest risk of carrying a fetus having said abnormality, B) determining a gestational age discrepancy value of the pregnant patient by calculating a difference between gestational age as determined by two methods, the two methods being i) last menstrual period date of the patient, and ii) biometric measurement of the fetus carried by the patient, C) determining in a sample of said pregnant patient's blood, a concentration of a biochemical marker indicative of said fetal abnormality, D) calculating a first probability that the gestational age discrepancy value and the concentration of the marker form part of a multivariate Gaussian distribution of gestational age discrepancy values and marker concentrations found in pregnancies with said fetal abnormality, E) calculating a second probability that the gestational age discrepancy value and the concentration of the marker form part of a multivariate Gaussian distribution of gestational age discrepancy values and marker concentrations found in unaffected pregnancies, F) calculating a likelihood ratio, said likelihood ratio being the ratio of said first probability and said second probability, and G) assessing the antenatal risk for said abnormality in the fetus carried by the patient by modifying the patient's pretest risk by the likelihood ratio.

4. The method according to claim 3 wherein said fetal abnormality is selected from the group consisting of Trisomy 18, and Open Spina Bifida.

5. The method according to claim 3 wherein said biochemical marker is selected from the group consisting of intact human chorionic gonadotropin (hCG), hCG alpha subunit, hCG free beta subunit, alphafetoprotein, pregnancy associated plasma protein A, unconjugated estriol, inhibin, progesterone, 16-alpha-hydroxy-dehydroepiandrosterone sulfate and dehydroepiandrosterone sulfate.

6. The method according to claim 1 wherein either of the two methods for determining gestational age indicates that the gestational age is 8–22 weeks.

7. The method according to claim 3 wherein either of the two methods for determining gestational age indicates that the gestational age is 8–22 weeks.

* * * * *